United States Patent
Kim et al.

(10) Patent No.: US 9,108,198 B2
(45) Date of Patent: Aug. 18, 2015

(54) MICROFLUIDIC APPARATUS

(71) Applicant: Samsung Electronics Co., Ltd., Suwon-si, Gyeonggi-do (KR)

(72) Inventors: Minseok S. Kim, Yongin-si (KR); Hui-sung Moon, Seoul (KR); Jong-myeon Park, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 20 days.

(21) Appl. No.: 14/052,464

(22) Filed: Oct. 11, 2013

(65) Prior Publication Data

US 2014/0341788 A1 Nov. 20, 2014

(30) Foreign Application Priority Data

May 20, 2013 (KR) .................. 10-2013-0056616

(51) Int. Cl.
*B01L 3/00* (2006.01)
*G01N 21/07* (2006.01)

(52) U.S. Cl.
CPC ... *B01L 3/502753* (2013.01); *B01L 2300/0803* (2013.01); *B01L 2300/0858* (2013.01); *B01L 2300/0864* (2013.01); *B01L 2300/0874* (2013.01); *B01L 2400/0409* (2013.01); *B01L 2400/0677* (2013.01); *B01L 2400/086* (2013.01); *G01N 21/07* (2013.01)

(58) Field of Classification Search
CPC .................. B01L 3/502753; B01L 2300/0864; B01L 2300/0874; B01L 2300/0803; B01L 2400/0677; B01L 2300/0858; B01L 2400/086; B01L 2400/0409; G01N 21/07
USPC ......................................................... 422/502
See application file for complete search history.

(56) References Cited

U.S. PATENT DOCUMENTS

| 7,445,766 B2 * | 11/2008 | Santini et al. ................ 424/9.1 |
| 2009/0238724 A1 | 9/2009 | Yamamoto et al. |
| 2010/0050751 A1 * | 3/2010 | Lee ............................. 73/64.56 |
| 2011/0176963 A1 * | 7/2011 | Kim et al. ..................... 422/68.1 |

FOREIGN PATENT DOCUMENTS

| KR | 1020080089835 A | 10/2008 |
| KR | 1020100087923 A | 8/2010 |
| KR | 1020110057416 A | 6/2011 |
| KR | 1020120093636 A | 8/2012 |

* cited by examiner

*Primary Examiner* — Lore Jarrett
(74) *Attorney, Agent, or Firm* — Leydig, Voit & Mayer, Ltd.

(57) ABSTRACT

Provided is a microfluidic apparatus that is mounted on a rotation driver and induces a flow of a fluid due to a centrifugal force, the microfluidic apparatus including: a separation unit that separates a target cell from a sample; a recovery chamber that is connected to the separation unit through a recovery channel and accommodates the target cell obtained by the separation; and an inclined portion that is disposed in the recovery chamber and tilted toward a bottom of the recovery chamber along a direction of the centrifugal force.

14 Claims, 10 Drawing Sheets

MICROFLUIDIC APPARATUS

CROSS-REFERENCE TO RELATED APPLICATIONS

This application claims the benefit of Korean Patent Application No. 10-2013-0056616, filed on May 20, 2013, in the Korean Intellectual Property Office, the entire disclosure of which is hereby incorporated by reference.

BACKGROUND

1. Field

The present disclosure relates to microfluidic apparatuses, and more particularly, to microfluidic apparatuses for separating a target cell from a biological sample.

2. Description of the Related Art

Most cancer-related deaths are due to metastasis to a tissue or organ located far from a point where a tumor originates. Thus, discovery of a metastasis at an early stage is a critical factor that determines survival probability. Early detection and monitoring development of a tumor are deemed as key factors in successfully treating cancer patients. A histopathology-based diagnosis is used to detect cancer. The histopathology-based diagnosis is a technique for diagnosing a cancer using a tissue sample obtained from a biopsy specimen. However, a biopsy specimen only provides information about the tissue contained in the biopsy specimen, such that a biopsy specimen may not generally be used to identify tumor metastasis. Accordingly, the use of histopathology in diagnosing or monitoring tumors, especially metastasized tumors, has many limitations.

Circulating tumor cells (CTCs) can be identified in patients before a tumor is originally detected, and CTCs may play an important factor in early diagnosing cancer. In addition, since cancer may spread through blood, CTCs may be a marker for identifying cancer metastasis. In addition, when CTCs can be detected after a tumor is removed by a surgical operation, the possibility of recurrence of cancer is very high. However, since the amount of CTCs in blood may be very small and since CTCs are very fragile, it is difficult to correctly quantify CTCs. Accordingly, there is a need to develop a diagnosis method with high sensitivity in detecting CTCs, cancer cells, or cancer stem cells present in patients.

Red blood cells, white blood cells/circulating tumor cells, or a serum may be manually separated from a density gradient in order to isolate CTCs, cancer cells, or cancer stem cells. However, a layer of white blood cells/CTCs is very thin, and thus, the layer of white blood cells/CTCs based on the density gradient is difficult to manually separate. Also, separation reproducibility largely depends on the ability of the person performing the separation.

SUMMARY

Provided are microfluidic apparatuses designed to improve a recovery rate of a target cell separated from a sample. Additional aspects will be set forth in part in the description which follows and, in part, will be apparent from the description, or may be learned by practice of the presented embodiments.

According to an aspect of the present invention, a microfluidic apparatus that is mounted on a rotation driver and induces a flow of a fluid due to a centrifugal force includes: a separation unit that separates a target cell from a sample; a recovery chamber that is connected to the separation unit through a recovery channel and accommodates the target cell obtained by the separation; and a structure with an inclined surface portion (hereinafter "inclined portion") that is disposed in the recovery chamber and tilted toward a bottom of the recovery chamber along a direction of the centrifugal force. The inclined portion may be disposed at a location corresponding to the recovery channel. The inclined portion may have a width greater than or equal to a width of the recovery channel.

The microfluidic apparatus may further include an upper plate and a lower plate forming an upper wall and a lower wall of the recovery chamber, respectively. The inclined portion may be disposed on the upper plate. The microfluidic apparatus may further include an upper plate and a lower plate forming an upper wall and a lower wall of the recovery chamber, respectively, and a partition plate forming a side wall of the recovery chamber. The inclined portion may be disposed on the partition plate. The microfluidic apparatus may further include a cover that covers an upper portion of the recovery chamber and is removable so as to open the upper portion of the recovery chamber. The microfluidic apparatus may further include an upper plate forming an upper wall of the recovery chamber. A connection port may be disposed in the upper plate and connect with the recovery chamber. The cover may be removably coupled to the upper plate so as to cover the connection port. The cover may have a groove recessed from a bottom surface thereof, and one end of the groove may extend to an edge of the microfluidic apparatus. The inclined portion may extend from the bottom surface of the cover and may be located inside the recovery chamber through the connection port.

The separation unit may include a sample chamber supplying a fluid containing a target material in which fine beads are bound to the target cell in the sample, and a separation chamber that accommodates a density gradient medium (DGM) having a lower density than that of the target material and receives the fluid from the sample chamber to separate the target material from the fluid by using a density difference. The target cell may include a circulating tumor cell (CTC), a cancer stem cell, or a cancer cell.

According to another aspect of the present invention, a microfluidic apparatus that is mounted on a rotation driver and induces a flow of a fluid due to a centrifugal force includes: a separation unit that separates a target cell from a sample; a recovery chamber that is connected to the separation unit through a recovery channel and accommodates the target cell obtained by the separation; and a cover that covers an upper portion of the recovery chamber and is removable so as to open the upper portion of the recovery chamber. The microfluidic apparatus may further include an upper plate forming an upper wall of the recovery chamber. A connection port may be disposed in the upper plate, and connected with the recovery chamber. The cover may be removably coupled to the upper plate so as to cover the connection port. The cover may have one or more grooves recessed in a bottom surface thereof, and one end of the grooves may extend to an edge of the microfluidic apparatus.

The microfluidic apparatus may further include an inclined portion that is disposed in the recovery chamber so as to guide the target cell, which is introduced into the recovery chamber through the recovery channel, towards a bottom of the recovery chamber. The inclined portion may extend from the bottom surface of the cover and may be located inside the recovery chamber through the connection port.

The separation unit may include a sample chamber supplying a fluid containing a target material in which fine beads are bound to the target cell in the sample, and a separation chamber that accommodates a density gradient medium (DGM)

having a lower density than that of the target material and receives the fluid from the sample chamber to separate the target material from the fluid by using a density difference. The target cell may include a circulating tumor cell (CTC), a cancer stem cell, or a cancer cell.

BRIEF DESCRIPTION OF THE DRAWINGS

These and/or other aspects will become apparent and more readily appreciated from the following description of the embodiments, taken in conjunction with the accompanying drawings, of which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Figure 1:
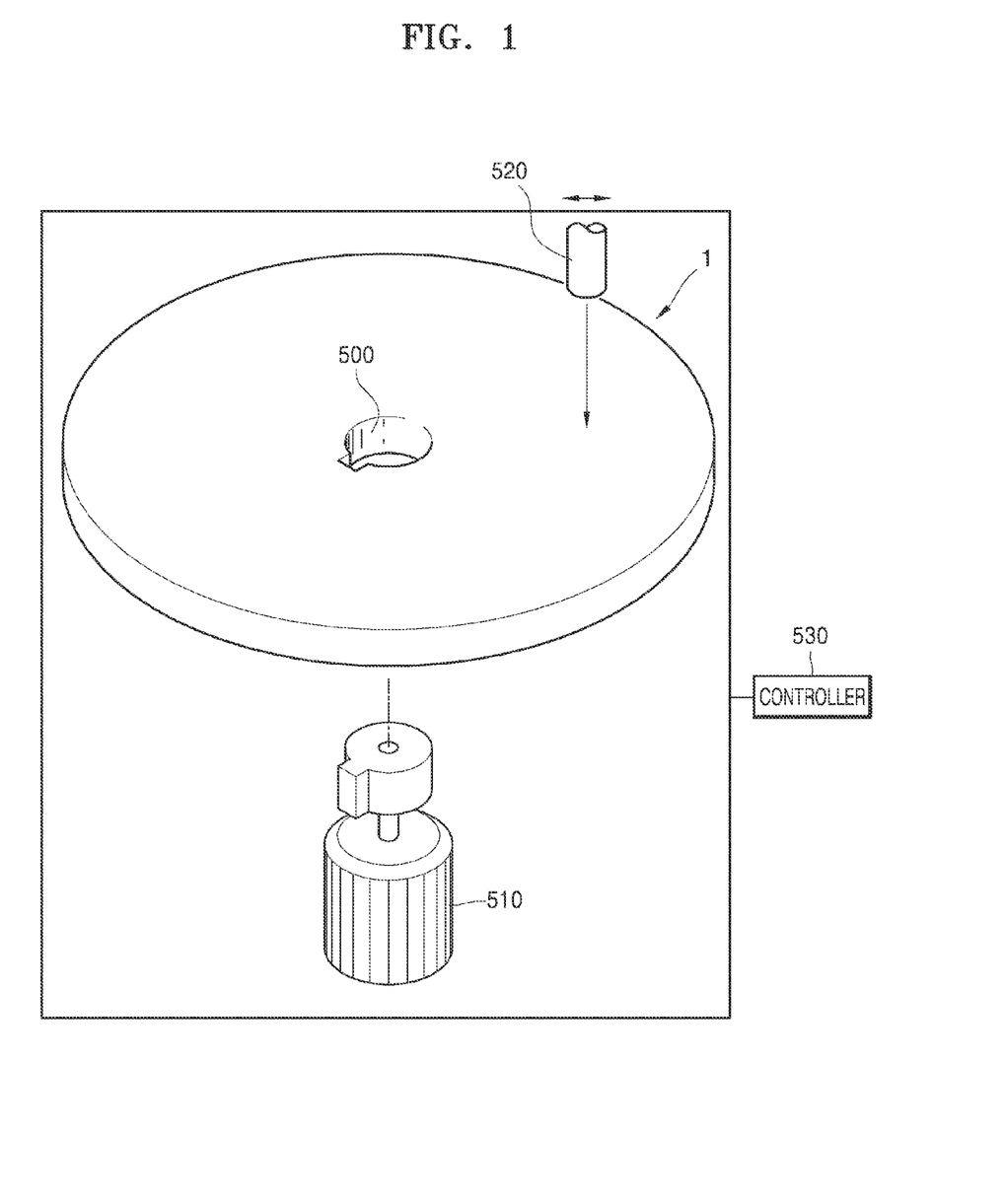
FIG. 1 is a schematic diagram of a target cell enrichment system.

FIG. 1 is an example of a target cell enrichment system using a microfluidic apparatus 1. Referring to FIG. 1, the system includes a rotation driver 510, an electromagnetic wave generator 520, and a mounting portion 500 for mounting the microfluidic apparatus 1 on to the rotation driver 510. The rotation driver 510 rotates the microfluidic apparatus 1 to provide a centrifugal force that causes centrifugation of a sample and movement of a fluid. The rotation driver 510 stops the microfluidic apparatus 1 at a predetermined location so that valves face the electromagnetic wave generator 520. The electromagnetic wave generator 520 operates the valves of the microfluidic apparatus 1, e.g., by irradiating laser beams. The electromagnetic wave generator 520 may move in a radial direction of the microfluidic apparatus 1. The rotation driver 510 may include a motor drive device (not shown) that controls an angular position of the microfluidic apparatus 1 so as to align the valves with the electromagnetic wave generator 520. For example, the motor drive device may use a stepper motor or a direct current (DC) motor. Reference numeral 530 denotes a controller for controlling an enrichment process.

Figure 2:
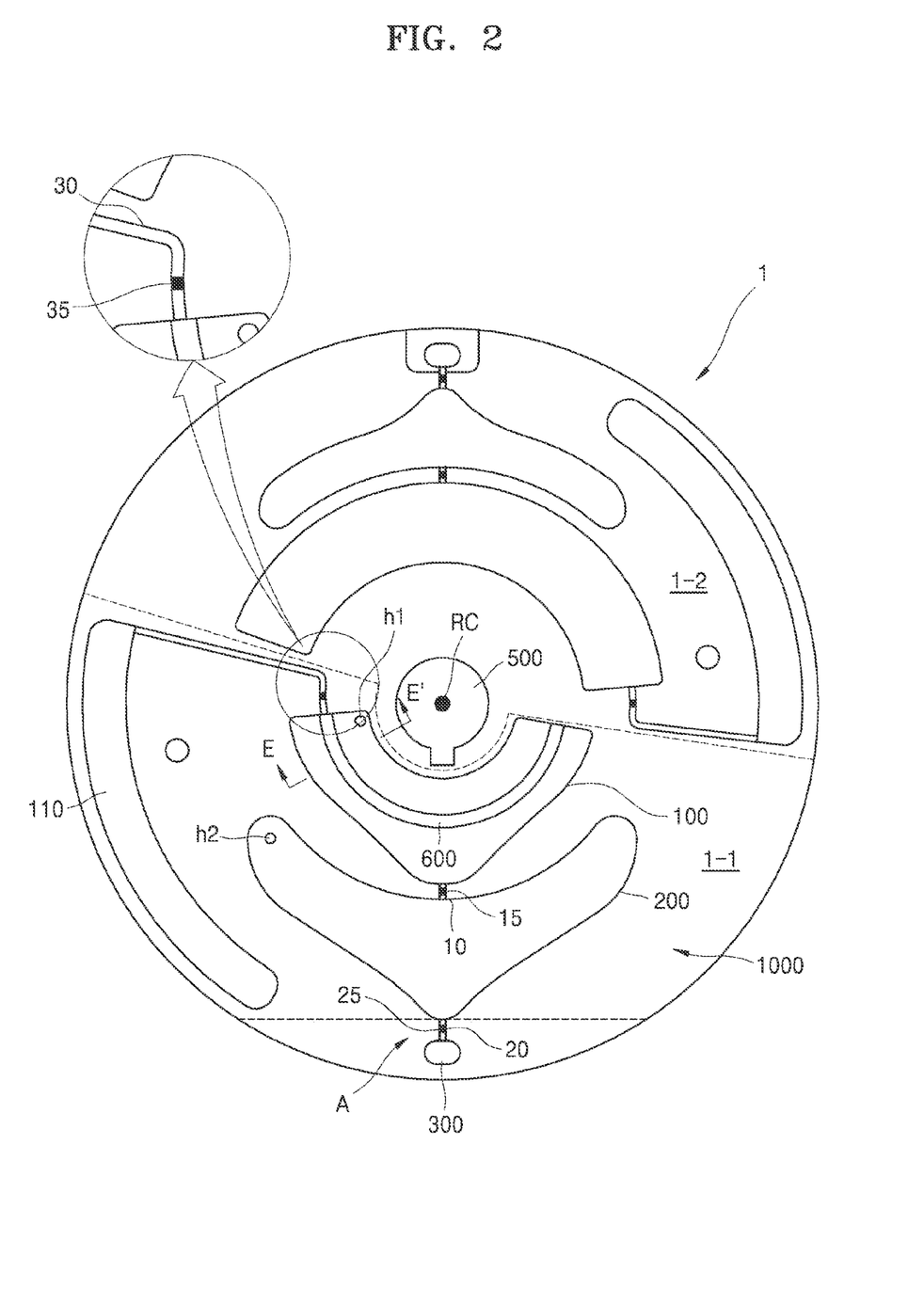
FIG. 2 illustrates a configuration of a microfluidic apparatus.

FIG. 2 illustrates a configuration of a microfluidic apparatus 1 according to an embodiment of the present invention. The microfluidic apparatus 1 according to the present embodiment induces a flow of a fluid contained therein due to a centrifugal force. The microfluidic apparatus 1 includes a microfluidic structure for providing a space for accommodating the fluid and a path along which the fluid flows. For example, the microfluidic apparatus 1 may have a rotatable disk shape, but is not limited thereto.

The microfluidic apparatus 1 may be formed of a plastic material such as acryl or polydimethylsiloxane (PDMS) which may be molded easily and has a biologically inactive surface. However, the present invention is not limited thereto, and the microfluidic apparatus 1 may be formed of any material having chemical and biological stability, optical transparency, and mechanical processability. The microfluidic apparatus 1 may include a plurality of plates. An engraved structure corresponding to a chamber or a channel is formed in a surface of a plate that faces another plate, and the plates are joined together to provide a space for receiving the fluid and the fluid path in the microfluidic apparatus 1. The microfluidic apparatus 1 may have a two-plate structure including an upper plate and a lower plate, or a three-plate structure including an upper plate, a lower plate, and a partition plate interposed therebetween to define the microfluidic structure. The plates may be joined using various methods, such as attachment using an adhesive or dual adhesive tape or welding using ultrasonic waves or a laser.

The microfluidic apparatus 1 may include one or more microfluidic structures. For example, the microfluidic apparatus 1 may be divided into a plurality of regions, each region having a microfluidic structure which operates independently of the other. In the microfluidic apparatus 1 according to the present embodiment, the microfluidic structures are provided in two regions 1-1 and 1-2. Since the microfluidic structures provided in the two regions 1-1 and 1-2 are substantially the same as each other, only the microfluidic structure in the region 1-1 will be described in more detail.

Referring to FIG. 2, the microfluidic apparatus 1 has a mounting portion 500 at its rotation center RC so that it is mounted on to the rotation driver 510. The microfluidic apparatus 1 includes a separation unit 1000 and a recovery chamber 300. The separation unit 1000 is disposed on the outside in a radial direction from the rotation center RC and separates a target cell from a biological sample using a centrifugal force. The recovery chamber 300 is disposed outside the separation unit 1000 and collects the target cell. The separation unit 1000 includes a sample chamber 100 and a separation chamber 200 connected to each other through a sample channel 10. The separation chamber 200 is connected to the recovery chamber 300 through a recovery channel 20. A sample valve 15 and a recovery valve 25 are disposed in the sample channel 10 and the recovery channel 20, respectively.

The sample chamber 100 supplies a fluid containing a target material, e.g., a target cell-fine bead complex. In the sample chamber 100, a target cell contained in the sample and fine beads contact each other, and the fine beads adhere to the target cell to form the target cell-fine bead complex. For example, the fine beads may be solid microbeads, magnetic beads, gel beads, or polymer microbeads. In one embodiment, the sample chamber 100 may include an inlet hole h1 for loading a sample. The fine beads may be introduced into the sample chamber 100 through the inlet hole h1 prior to separation of the target cell from the sample. The inlet hole h1 may be disposed in an upper plate (not shown). When the microfluidic apparatus 1 is manufactured for a predetermined task, fine beads suitable for the task may be introduced in the sample chamber 100 during the procedure of manufacturing the microfluidic apparatus 1.

The target cell may include a circulating tumor cell (CTC), a cancer stem cell, or a cancer cell. For example, the target cell may include a cell in a cancer or tumor selected from the group comprising bladder cancer, breast cancer, cervical cancer, cholangiocarcinoma, colorectal cancer, endometrial cancer, esophageal cancer, gastric cancer, head and neck cancer, kidney cancer, liver cancer, lung cancer, nasopharyngeal cancer, ovarian cancer, pancreatic cancer, gallbladder cancer, prostate cancer, thyroid cancer, osteosarcoma, rhabdomyosarcoma, synovial sarcoma, Kaposi's sarcoma, leiomyosarcoma, malignant fibrous histiocytoma, fibrosarcoma, adult T-cell leukemia, lymphoma, multiple myeloma, glioblastoma/astrocytoma, melanoma, mesothelioma, and Wilms' tumor, but not be limited thereto.

The sample may include any of a number of biological samples as long as the target cell exists therein. For example, the biological sample may be selected from the group comprising a biopsy sample, a tissue sample, a cell suspension having a separated cell suspended in a liquid medium, a cell culture, and any combinations thereof, but may not be limited thereto. The sample may also be selected from the group comprising blood, marrow fluid, saliva, lacrimal fluid, urine, semen, mucous fluid, and any combinations thereof, but may not be limited thereto. For example, in order to separate CTCs, blood may be used as the sample.

At least one ligand specific to a surface marker of a target cell is bound to the fine beads. The fine beads serve to increase the density of the target cell by binding to the target cell. The fine beads may have a density value which may cause a density difference between the target cell and another cell in the sample. For example, when the biological sample is blood containing a cancer cell as the target cell, and since white blood cells (WBCs) and red blood cells (RBCs) have densities of about 1.07 $g/cm^3$ and about 1.1 $g/cm^3$, respectively, fine beads with an appropriate density may be selected in consideration of such densities. For example, the fine particles may be selected from the group comprising polystyrene particles, polymethylmethacrylate particles, latex particles, acrylonitril-butadiene-styrene copolymer (ABS) particles, and a complex thereof, but may not be limited thereto. A diameter of the fine beads may vary according to the type of the target cell to be separated and the type of beads to be used. The diameter may be, for example, from about 1 nm to about 100 μm, or from about 10 nm to about 10 μm.

The surface marker may include a marker selected from the group comprising protein, sugar, lipid, nucleic acid, and any combinations thereof, but may not be limited thereto. For example, the surface marker may be a protein, e.g., an antigen, which is specifically expressed in a cancer or tumor cell and is displayed in a cell membrane, such as epithelial cell adhesion molecule (EpCAM), c-Met, cytokeratines, CD45, Human Epidermal Growth Factor Receptor 2 (Her2), or any combinations thereof. In addition, the at least one ligand specific to the surface marker may be an antibody which may bind specifically to an antigenic protein.

Referring again to FIG. 2, the separation chamber 200 separates a target material from a fluid supplied from the sample chamber 100 and includes a density gradient medium (DGM). The DGM is used to separate a target material from a fluid by using a density gradient. The DGM has a density that is less than that of the target material and greater than a fluid other than the target material. Thus, during centrifugation, the DGM is interposed between the fluid and the target material so as to separate the target material from the fluid. The separation chamber 200 may include an inlet hole h2 through which the DGM is loaded. The inlet hole h2 may be disposed in an upper plate (not shown). When the microfluidic apparatus 1 is to be used for a particular task, the DGM suitable for the task can be introduced in the separation chamber 200 in advance, for example, during the procedure of manufacturing the microfluidic apparatus 1.

The separation chamber 200 is disposed outside the sample chamber 100 in a radial direction away from the rotation center RC so that the fluid flows from the sample chamber 100 to the separation chamber 200 due to a centrifugal force. In other words, the separation chamber 100 is located further from the RC than the sample chamber 200, and may be generally aligned with the separation chamber 200 in a radial direction from the RC, such that the sample chamber 100 is positioned generally between the RC and the separation chamber 200. The separation chamber 200 is connected to the sample chamber 100 by channel 10. In the separation chamber 200, the target material and the fluid are separated from each other by the DGM interposed therebetween. The target material is collected into a lowermost layer of the separation chamber 200, that is, an outermost material layer in the radial direction away from the rotation center RC.

The recovery chamber 300 is disposed outside the separation chamber 200 in a radial direction away from the rotation center RC. In other words, the recovery chamber 300 is located further from the RC than the separation chamber 200, and may be generally aligned in a radial direction with the separation chamber 200, such that the separation chamber 200 is generally positioned between the recovery chamber 300 and the sample chamber 100. The recovery chamber 300 is connected to the separation chamber 200 via the recovery channel 20. In the separation chamber 200, the target material is collected into the lowermost region or layer of the separation chamber 200. When the recovery channel 20 is opened by the recovery valve 25, the target material is introduced into the recovery chamber 300 due to a centrifugal force.

As shown in FIG. 2, the separation unit 1000 may further include a waste chamber 110 disposed outside of the sample chamber 100 in a radial direction away from the rotation center RC. The waste chamber 110 is also connected to the sample chamber 100 through a waste channel 30 (see inset of FIG. 2). A waste valve 35 is disposed in the waste channel 30 to control the flow of a fluid.

Before transporting a fluid having a target material formed in the sample chamber 100 to the separation chamber 200, a portion of the fluid in the sample chamber 100 may be removed. For example, after forming a target material containing a target cell bound to fine beads within the sample chamber 100, centrifugation is performed on a fluid containing the target material to discard an upper material layer located at an upper portion of the target cell into the waste chamber 110 and then transport the remaining fluid and the target material to the separation chamber 200. If a blood sample containing CTCs is subjected to centrifugation within the sample chamber 100, a plasma layer may be separated as an uppermost layer that is closest to the rotation center RC, and pumped into the waste chamber 110.

The sample valve 15, the separation valve 25, and the waste valve 35 may be microfluidic valves. The sample valve 15, the separation valve 25, and the waste valve 35 may also be normally closed valves that close the sample channel 10, the separation channel 20, and the waste channel 30, respectively, so as to prevent fluid from flowing before the valve is actuated.

Figure 3A:
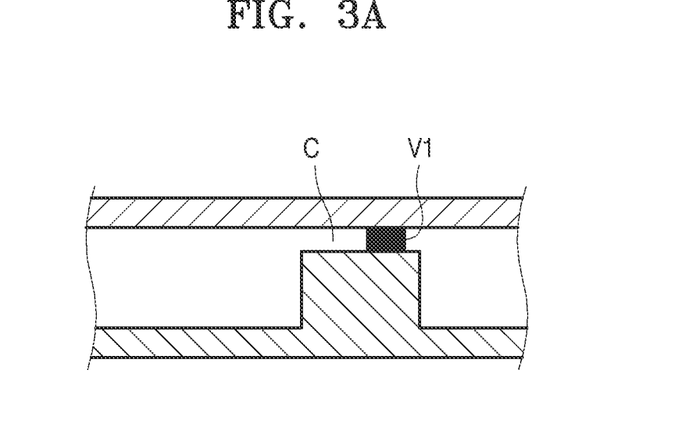
FIGS. 3A and 3B are cross-sectional views of a normally closed valve.
Figure 3B:
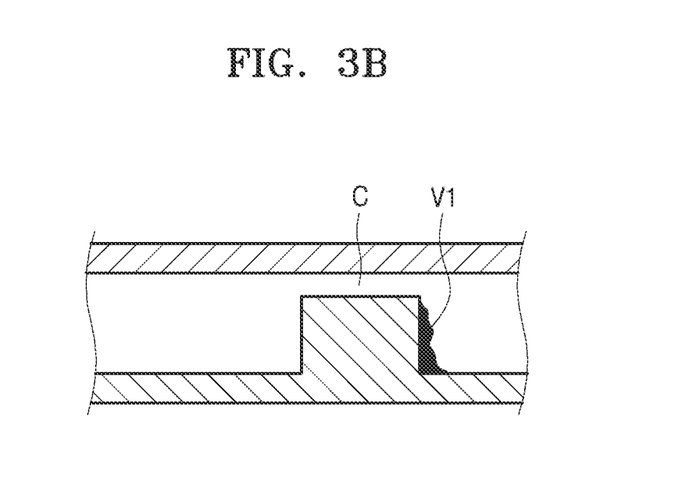

FIGS. 3A and 3B are cross-sectional views showing an example of a normally closed valve. The normally closed valve may include a valve material V1 that is solid at room temperature. The valve material V1 exists in a channel C in a solid state to block the channel C as shown in FIG. 3A. As shown in FIG. 3B, the valve material V1 melts at a high temperature and moves to a space in the channel C and then coagulates again while the channel C is opened. An energy irradiated from outside the microfluidic apparatus 1 may include, for example, an electromagnetic wave, and an external energy source may be a laser light source emitting laser beams or a light emitting diode or a Xenon lamp emitting visible rays or infrared rays. When the external energy source is the laser light source, it may include at least one laser diode. The external energy source may be selected according to a wavelength of the electromagnetic wave that can be absorbed by exothermic particles contained in the valve material V1. The valve material V1 may be a thermoplastic resin such as cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF). In addition, a phase change material that is in a solid state at room temperature may be used as the valve material V1. The phase change material may be wax. When the wax is heated, the wax melts into a liquid state and expands. The wax may be paraffin wax, microcrystalline wax, synthetic wax, or natural wax. The phase change material may be a gel or thermoplastic resin. The gel may be polyacrylamides, polyacrylates, polymethacrylates, or polyvinylamides. In the valve material V1, a plurality of fine exothermic particles which absorb electromagnetic wave energy to generate heat may be dispersed. Each of the fine exothermic particles may have a diameter of about 1 nm to about 100 µm so as to freely pass through the channel C having a depth of about 0.1 mm and a width of about 1 mm. When the electromagnetic wave energy is supplied to the fine exothermic particles through laser beams, for example, the temperature of the fine exothermic particles rises rapidly to generate heat, and the fine exothermic particles are evenly dispersed in the wax. The fine exothermic particles may have a core containing a metal component, and a hydrophobic surface structure. For example, the fine exothermic particles may have a molecular structure including a core formed of iron (Fe) and a plurality of surfactants that are bound to and surround the core. The fine exothermic particles may be dispersed and stored in carrier oil. The carrier oil may also be hydrophobic so that the fine exothermic particles having a hydrophobic surface structure may be evenly dispersed. The carrier oil in which the fine exothermic particles are dispersed is mixed into the melted phase change material, and the mixture is injected into the channel C and solidified to block the channel C. The fine exothermic particles are not limited to the above-described polymer particles, and may be quantum dots or magnetic beads. Alternatively, the fine exothermic particles may be fine metal oxide, such as aluminum oxide ($Al_2O_3$), titanium oxide ($TiO_2$), tantalum oxide ($Ta_2O_3$), iron oxide ($Fe_2O_3$), $Fe_3O_4$, or hafnium oxide ($HfO_2$). On the other hand, the normally closed valve does not necessarily include the fine exothermic particles, and may be formed of only the phase change material without the use of the fine exothermic particles.

Figure 4:
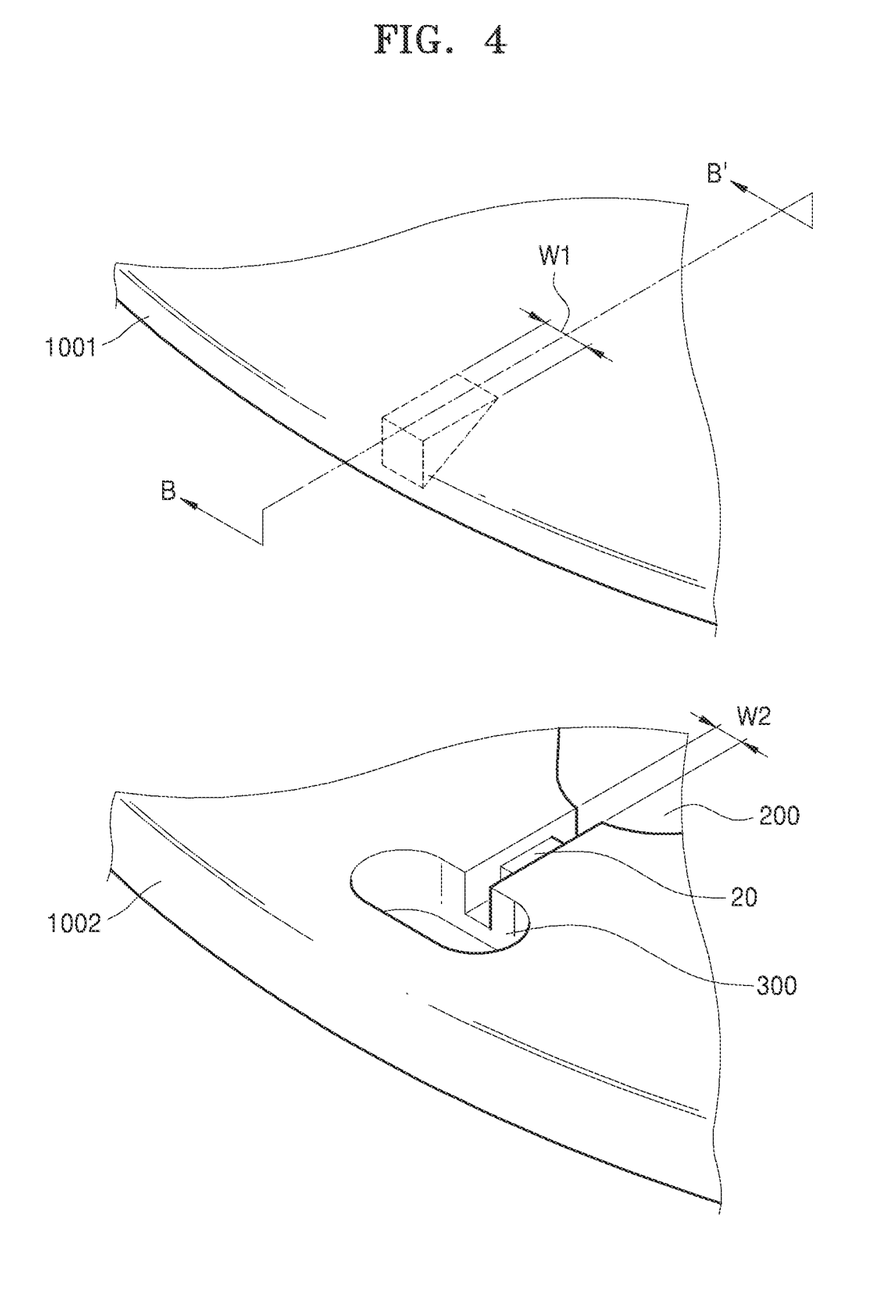
FIG. 4 is a detailed partial exploded perspective view of a portion A in the microfluidic apparatus of FIG. 2.
Figure 5:
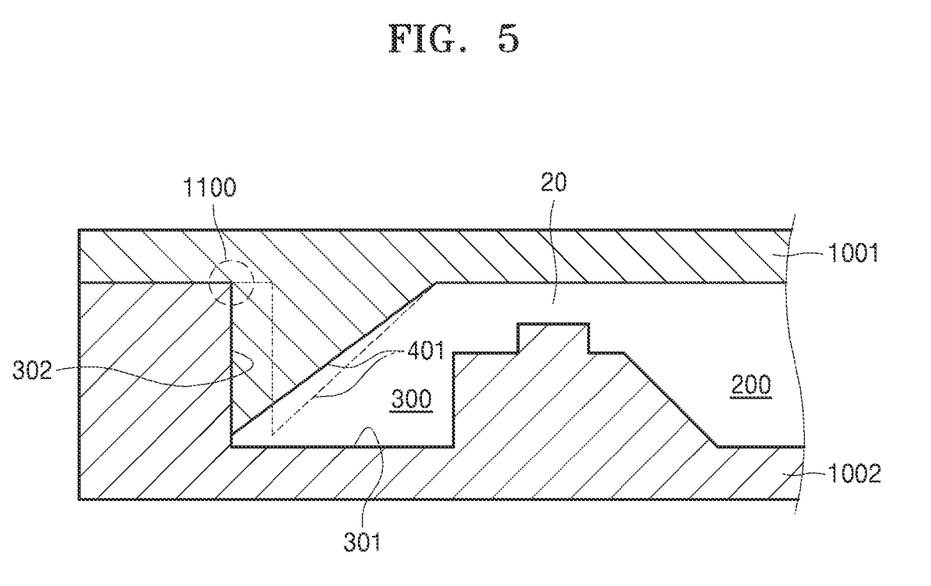
FIG. 5 is an example of a cross-sectional view taken along line B-B' of FIG. 4.

FIG. 4 is a partial exploded perspective view of a portion A in the microfluidic apparatus of FIG. 2. FIG. 5 is an example of a cross-sectional view taken along line B-B' of FIG. 4. Referring to FIGS. 4 and 5, an inclined portion 401 is formed at a location corresponding to the entrance or inlet of the recovery channel 20 to the recovery chamber 300. The inclined portion 401 guides a target material that is introduced into the recovery chamber 300 through the recovery channel 20 towards a bottom 301 of the recovery chamber 300.

In one embodiment, the microfluidic apparatus 1 has a two-plate structure including an upper plate 1001 and a lower plate 1002. The lower plate 1002 includes an engraved structure that provides spaces for forming the recovery chamber 300, the separation chamber 200, the recovery channel 20, the sample chamber (100 in FIG. 2), the waste chamber (110 in FIG. 2), the sample channel (10 in FIG. 2), and a waste channel (30 in FIG. 2). The upper plate 1001 may be bonded to the lower plate 1002 to thereby realize the microfluidic apparatus 1. In this structure, the upper and lower plates 1001 and 1002 form upper and lower walls of the recovery chamber 300, respectively. The inclined portion 401 may project down from a bottom surface of the upper plate 1001. The inclined portion 401 is also tilted toward the bottom 301 along the radial direction away from the rotation center RC, i.e., along the direction of a centrifugal force in the recovery chamber 300. Thus, the top part of the inclined portion (nearest the upper wall of the chamber) is closer to the RC than the bottom part of the inclined portion. In other words, the inclined portion 401 provides a surface or wall within the recovery chamber 300 positioned at an acute angle to the bottom surface of the chamber, with the top part of the surface or wall (nearest the upper wall of the chamber) being closer to the RC than the bottom part of the surface or wall. The inclined portion 401 may be disposed in the recovery chamber 300 at a location corresponding to the entrance of the recovery channel 20 and have a width W1 greater than a width W2 of the recovery channel 20. Thus, the inclined portion 401 may serve to effectively guide the target material, which is introduced into the recovery chamber 300 through the recovery channel 20, toward the bottom 301.

More specifically, the target material is transported from the separation chamber 200 to the recovery chamber 300 through the recovery channel by a centrifugal force produced due to rotation of the microfluidic apparatus 1. The target material that has passed through the recovery channel 20 strongly hits an outside wall 302 in the radial direction. That is, since the recovery channel 20 is located above the bottom 301 of the recovery chamber 300, the target material that has passed through the recovery channel 20 is directed toward a boundary 1100 between the upper and lower plates 1001 and 1002. Because the upper plate 1001 is coupled to the lower plate 1002 at the boundary 1100, there may be a fine slit in the boundary 1100. In the presence of the fine slit, the target material may leak into the slit due to a strong centrifugal force so it is difficult to extract the target material, thereby reducing a recovery rate of the target material. Thus, in the microfluidic apparatus 1 according to the present embodiment, the inclined portion 401 is disposed to guide the target material received into the recovery chamber 300 toward the bottom 301 of the recovery chamber 300 so that target material is then collected to the bottom 301. Thus, the target material may be extracted through an outlet hole (not shown) that penetrates the upper plate 1001 and connects with the recovery chamber 300 by using a tool such as a pipette, thereby improving the recovery rate of the target material. In this case, the outlet hole may be located outside the inclined portion 401.

While the inclined portion 401 extends to the outside wall 302 of the recovery chamber 300, the present invention is not limited thereto. The inclined portion 401 may have any titled shape that can guide the target material received into the recovery chamber 300 toward the bottom 301, and may not necessarily extend to the outside wall 302 in the radial direction. For example, as indicated by a dotted line in FIG. 5, the inclined portion 401 may be spaced apart from the outside wall 302.

Figure 6:
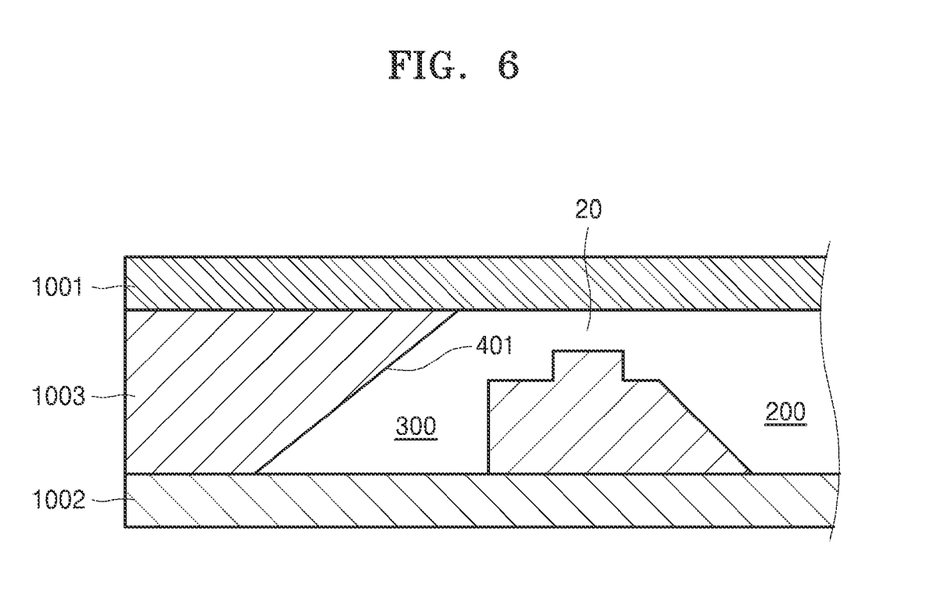
FIG. 6 is another example of a cross-sectional view taken along line B-B' of FIG. 4 wherein the microfluidic apparatus comprises three plates.

Although in the embodiment illustrated in FIGS. 4 and 5, the inclined portion 401 is disposed in the upper plate 1001, the present invention is not limited thereto. FIG. 6 is a cross-sectional view of another example of the microfluidic apparatus 1. Referring to FIG. 6, the microfluidic apparatus 1 has a three-plate structure including an upper plate 1001 and a lower plate 1002 separated from each other, and a partition plate 1003 sandwiched between the upper and lower plates 1001 and 1002. By coupling the partition plate 1003 to the upper and lower plates 1001 and 1002, a microfluidic structure including chambers and channels is defined. In this case, the upper and lower plates 1001 and 1002 form upper and lower walls of the recovery chamber 300, respectively, and the partition plate 1003 forms a side wall thereof. In the microfluidic apparatus 1 having the three-plate structure, the inclined portion 401 may be disposed on the partition plate 1003. Of course, in this structure as well, the inclined portion 401 may be disposed in the upper plate 1001.

As an approach to improving the recovery rate of the target material, a space used to access the recovery chamber 300 may be made large. To achieve this, the size of an outlet hole may be increased. However, in general, the size of the outlet hole is much smaller than the size of the recovery chamber 300 to prevent a fluid from leaking through the outlet hole during separation of the target material. Furthermore, the outlet hole may be closed using an adhesive tape during separation of the target material so as to prevent such a leakage. In this case, the adhesive tape may be torn due to a strong centrifugal force generated during the separation.

Figure 7:
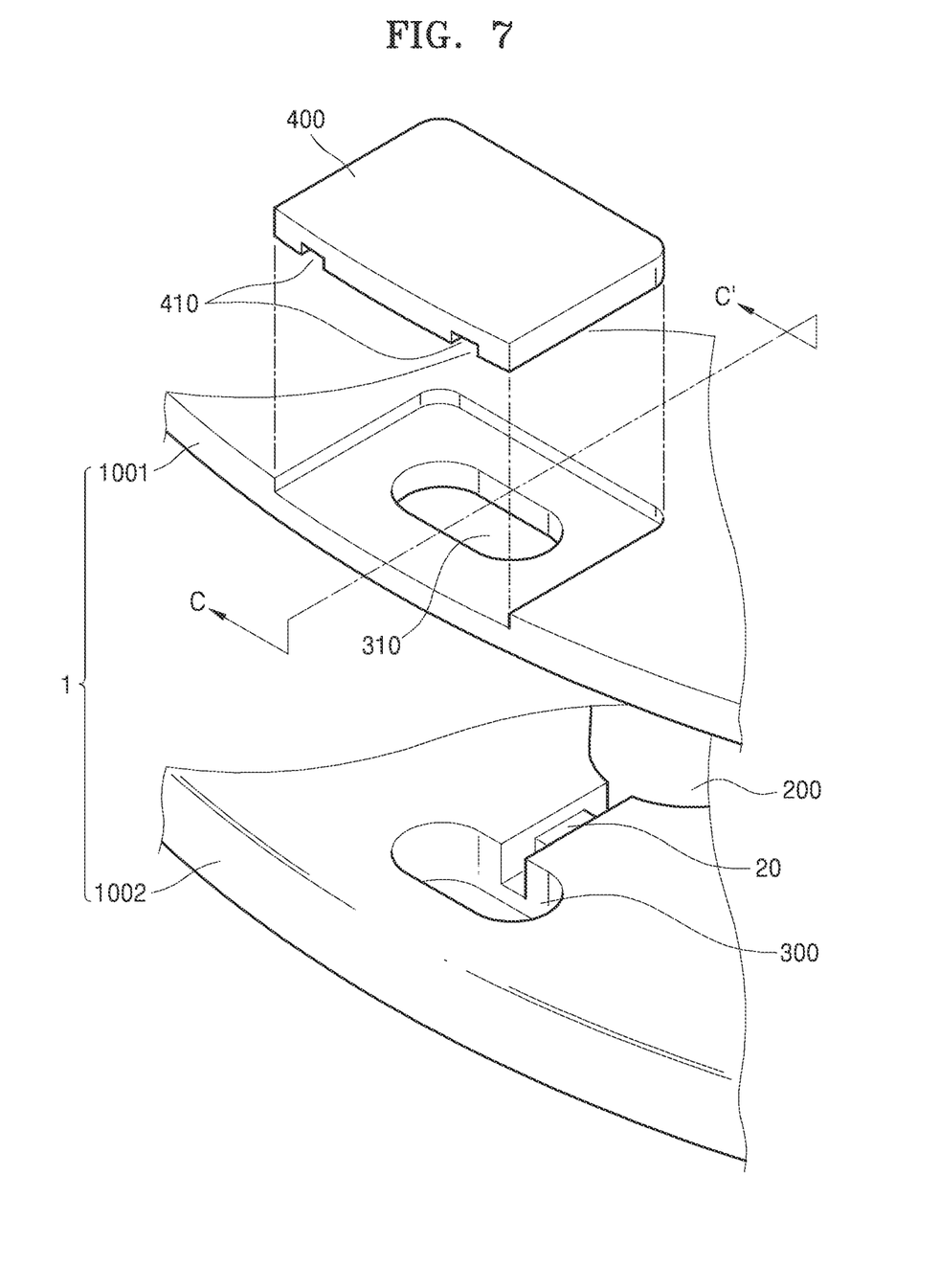
FIG. 7 is a partial exploded perspective view of a microfluidic apparatus.
Figure 8:
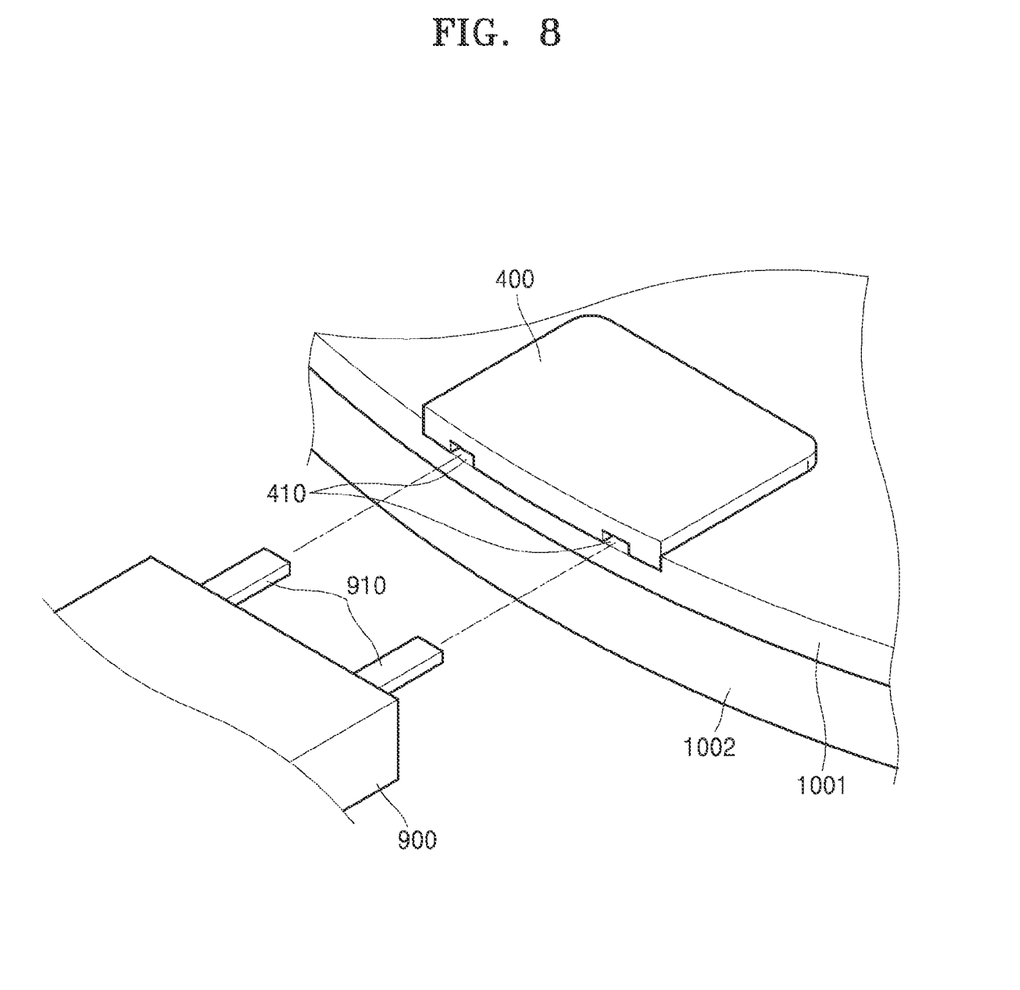
FIG. 8 is a perspective view illustrating a method of separating a cover of the microfluidic apparatus of FIG. 7.

FIG. 7 is a partial exploded perspective view of a microfluidic apparatus 1 according to another embodiment of the present invention. FIG. 8 is a perspective view illustrating a method of separating a cover 400 from the microfluidic apparatus 1 of FIG. 7. Referring to FIG. 7, the microfluidic apparatus 1 according to the present embodiment includes the cover 400 for opening the recovery chamber 300 in order to extract a target material collected in the recovery chamber 300. For example, a connection port 310 may be disposed in an upper plate 1001 forming an opening in the upper plate by which to access and connect with the recovery chamber 300, and the cover 400 may be coupled to the upper plate 1001 so as to cover the connection port 310. The cover 400 may be formed of the same material as that of the upper and lower plates 1001 and 1002, and bonded to the upper plate 1001 by adhesive tape. Since the size of the connection port 310 may be approximately equal to the size of the recovery chamber 300 in this structure, the entire recovery chamber 300 may be exposed if the cover 400 is removed. This structure makes it easy to extract a target material collected in the recovery chamber 300 with high efficiency by using a pipette, thereby improving a recovery rate of the target material.

The cover 400 has concave grooves 410 formed on a bottom surface thereof. The concave grooves 410 extend to an outer edge of the cover 400, and one end of each concave groove 410 is exposed to create a gap between the cover 400 and the upper plate 100 when the cover 400 is coupled to the upper plate 1001. In other words, the one end of the concave groove 410 extends to an outer edge of the microfluidic apparatus 1. For example, as shown in FIG. 8, insertion protrusions 910 of a separation tool 900 may be inserted into the corresponding concave grooves 410 and lifted up so as to facilitate detachment of the cover 400 from the upper plate 1001.

Although not shown in FIG. 7, the inclined portion 401 shown in FIG. 4 or 6 may be used in the microfluidic apparatus 1 of FIG. 7. In addition, the inclined portion 401 may be disposed on the cover 400.

Figure 9:
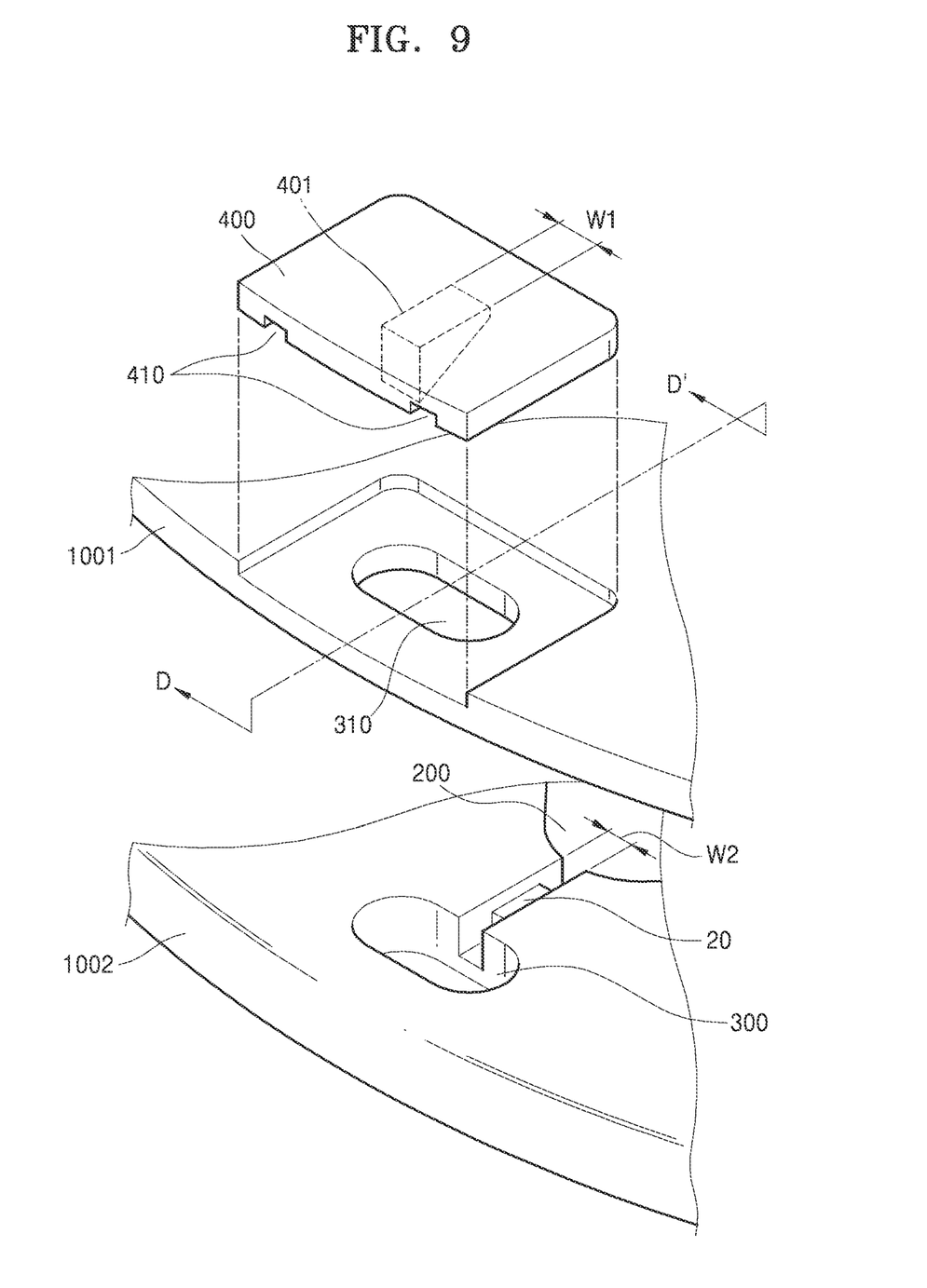
FIG. 9 is an partial exploded perspective view of a microfluidic apparatus.
Figure 10:
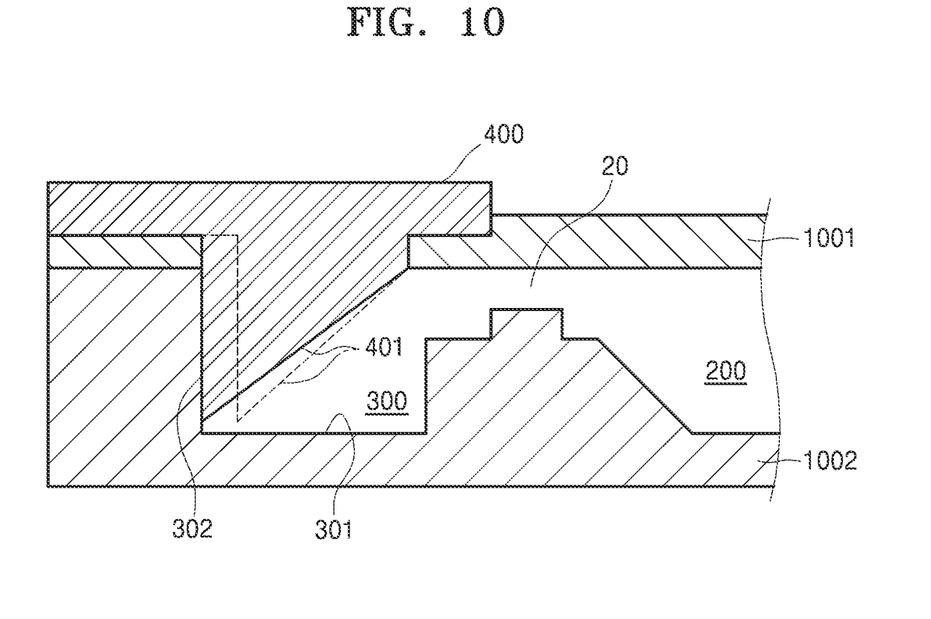
FIG. 10 is a cross-sectional view taken along line D-D' of FIG. 9.

FIG. 9 is an partial exploded perspective view of a microfluidic apparatus according to another embodiment of the present invention, and FIG. 10 is a cross-sectional view taken along line D-D' of FIG. 9. Referring to FIGS. 9 and 10, an inclined portion 401 is disposed on a bottom surface of a cover 400 so as to project downward. Although FIG. 10 shows that the inclined portion 401 extends to an outside wall 301 of the recovery chamber 300, the present invention is not limited thereto. For example, as indicated by a dotted line in FIG. 10, the inclined portion 401 may be spaced apart from the outside wall 302. The above-described structure allows a target material introduced into the recovery chamber 300 to be guided toward the bottom 301 of the recovery chamber 300, thereby facilitating easy extraction of the target material after removing the cover 400 and improving a recovery rate of the target material.

A method of enriching and separating a target cell using the microfluidic apparatus 1 having the above-described structure according to an embodiment of the present invention will now be described. In the present embodiment, a blood containing CTCs is used as a sample.

[Preparation]: About 5 mL of a blood containing CTCs as a target cell and more than about $1 \times 10^8$ of fine beads combined with an antibody that binds specifically to an antigen on the target cell are loaded into the sample chamber 100 through the inlet hole h1. In addition, an appropriately selected DGM is loaded into the separation chamber 200 through the inlet hole h2. For example, the DGM may be Ficoll, Percoll, polysaccharide, or sodium chloride (NaCl) solution. WBCs and CTCs having similar physical properties are isolated in an identical layer upon density gradient centrifugation. Thus, in the present embodiment, only cancer cells are separated from the blood by binding the fine beads to the CTCs to induce a density difference from the WBCs. For example, the fine beads may be melamine particles having a density of about 1.57 $g/cm^3$, which is greater than a density of about 1.05 to about 1.1 $g/cm^3$ of biological particles present in the blood.

[Formation of a target material (target cell-fine beads complex)]: After mounting the microfluidic apparatus 1 on to the rotation driver 510, the microfluidic apparatus 1 is repeatedly rotated clockwise or counterclockwise for a predetermined time so that the fine beads contacts and is bound to the target cell, thereby forming a target material in the sample chamber 100.

[Transporting of a fluid]: The electromagnetic wave generator 520 irradiates the sample valve 15 with electromagnetic waves such as laser beams in order to open the sample channel 10. Then, the valve material V1 melts so that the sample channel 10 is opened. Due to a centrifugal force generated upon rotation of the microfluidic apparatus 1, a fluid in the sample chamber 100 is transported to the separation chamber 200 that accommodates the DGM through the sample channel 10.

[Separation of the target material using a density gradient within the separation chamber 200]: The microfluidic apparatus 1 is rotated, for example, for about 10 minutes at a rate of, for example, 4000 r.p.m. Then, in the separation chamber 200, a sample is separated into a plurality of layers by density gradients of materials in the sample. For example, the sample may be divided into a DGM layer, a RBC layer, a WBC layer, and a plasma layer. Since the target material containing a target cell bound to a fine beads has the highest density, the target cell is separated from the WBC layer in the form of the target material and is located at a lowermost portion of the separation chamber 200, i.e., at an outermost portion in the radial direction from the rotation center RC. The DGM layer, the RBC layer, the WBC layer, and the plasma layer are arranged next to the target cell in this order toward the inside of the separation chamber 200.

[Recovery of a target material]: The electromagnetic wave generator 520 irradiates the recovery valve 25 with electromagnetic waves such as laser beams to thereby open the recovery channel 20. Upon rotating the microfluidic apparatus 1 again, the target material at the lowermost layer of the separation chamber 200 is conveyed to the recovery chamber 300 via the recovery channel 20 by a centrifugal force. Since the density and volume of the target material are greater than other cells in the blood, the target material may be separated through filtration. Thus, upon subsequent filtration, an enriched target material excluding the fluid may be obtained.

In the microfluidic apparatus 1 shown in FIGS. 4, 5, 6, 9, and 10, the inclined portion 401 is disposed to guide the target material in the recovery chamber 300 towards the bottom 301 of the recovery chamber 300. Thus, the target material that has passed through the recovery channel 20 is guided by the inclined portion 401 and collected to the bottom 301 of the recovery chamber 300. Thus, a recovery rate may be improved by reducing losses of the target material.

In addition, in the microfluidic apparatus 1 shown in FIGS. 7 through 10, an upper portion of the recovery chamber 300 may be opened by removing the cover 400, thereby allowing effective extraction of the target material from the recovery chamber 300 by using a pipette.

In the presence of the waste chamber 110, before the transporting of the fluid, centrifugation is performed on the blood in the sample chamber 100 by rotating the microfluidic apparatus 1. After the centrifugation, the blood in the sample chamber 100 is separated into a plasma layer, a WBC layer, a RBC layer, and a target material layer that are arranged in the radial direction. When the microfluidic apparatus 1 is stopped, the electromagnetic wave generator 520 irradiates the waste valve 35 with electromagnetic waves such as laser beams. Then, the valve material V1 melts so that the waste channel 30 is opened. By using a centrifugal force generated upon rotating the microfluidic apparatus 1, an upper material layer of the layers within the sample chamber 100, i.e., the plasma layer, is discharged into the waste chamber 110 through the waste channel 30. Then, the transporting of the fluid is performed.

As described above, the specific binding of fine beads and a target cell may depend on an antigen-antibody binding described above. A sample may contain various kinds of proteins and such proteins may prohibit the specific bond between the fine beads and the target cell. For example, binding between the fine beads and the target cell may be prevented when a protein that has a structure similar to that of an antigen is bound to a surface marker of a target cell in advance. In addition, binding between the fine beads and the target cell may be prevented when a protein that has a structure similar to that of an antibody is bound to a ligand of the fine beads. As such, proteins in a sample prevent the generation of a target cell-fine beads complex, thereby lowering the enrichment efficiency of the target cell. To prevent the decrease in enrichment efficiency, proteins in the sample may be removed from the sample before the fine beads are mixed with the sample.

In this regard, after a blood sample containing a CTC as a target cell is loaded into the sample chamber 100, the microfluidic apparatus 1 is mounted on the rotation driver 510 and is rotated, for example, for about five minutes at a rate of about 1000 to about 8000 r.p.m., e.g., about 3000 r.p.m. Then, in the sample chamber 100, the blood is separated into a plurality of layers due to a density difference. An RBC layer containing the heaviest RBCs is located at an outermost portion of the sample chamber 100. A target layer containing WBCs and the target cell, and a plasma layer as an upper material layer are arranged next to the RBC layer in this order. Since proteins in the blood excluding blood cells are lighter than the blood cells, they are disposed in the plasma layer. After stopping the rotation of the microfluidic apparatus 1, the electromagnetic wave generator 520 irradiates the waste valve 35 with electromagnetic waves, such as laser beams, in order to open the waste channel 30. Upon rotating the microfluidic apparatus 1 again, plasma is discharged into the waste chamber 110 by a centrifugal force. In this course, all or some of the proteins in the blood that may prohibit binding between the target cell and the fine beads are discharged into the waste chamber 110 together with the plasma.

For a subsequent process, the fine beads are loaded into the sample chamber 100, followed by the above-described operations such as formation of a target material (target cell-fine beads complex), the transporting of the fluid, separation of the target material using a density gradient within the separation chamber 200, and recovery of the target material. Although not shown in the drawings, the microfluidic apparatus 1 may further include a beads chamber for accommodating fine beads so that the fine beads are transported to the sample chamber 100 by a centrifugal force after discharging the plasma layer.

In the microfluidic apparatus 1, to discharge an upper material layer into the waste chamber 110 or to transport the target material into the separation chamber 200 after performing centrifugation to separate the sample in the sample chamber 100 into a plurality of layers by a density gradient, the microfluidic apparatus 1 is stopped from rotating and then the waste valve 35 or the sample valve 15 are opened. In this case, since the microfluidic apparatus 1 is not rotated at this time, a centrifugal force does not act on the sample in the sample chamber 100, and after some time elapses, the plurality of layers may be gradually mixed together due to molecular motions in the sample. Accordingly, the upper material layer may be mixed with the target layer containing the target cell, which decreases the enrichment efficiency, or the target cell may be discharged into the waste chamber 110 together with the upper material layer.

Referring again to FIG. 2, the sample chamber 100 may include a barrier wall 600 for at least partially restricting a flow of a fluid in the radial direction. The barrier wall 600 may occupy a portion of the width of the sample chamber 100 in a circumferential direction of the sample chamber 100. Also, the barrier wall 600 may occupy the entire width of the sample chamber 100 in the circumferential direction, as shown in FIG. 2.

Figure 11:
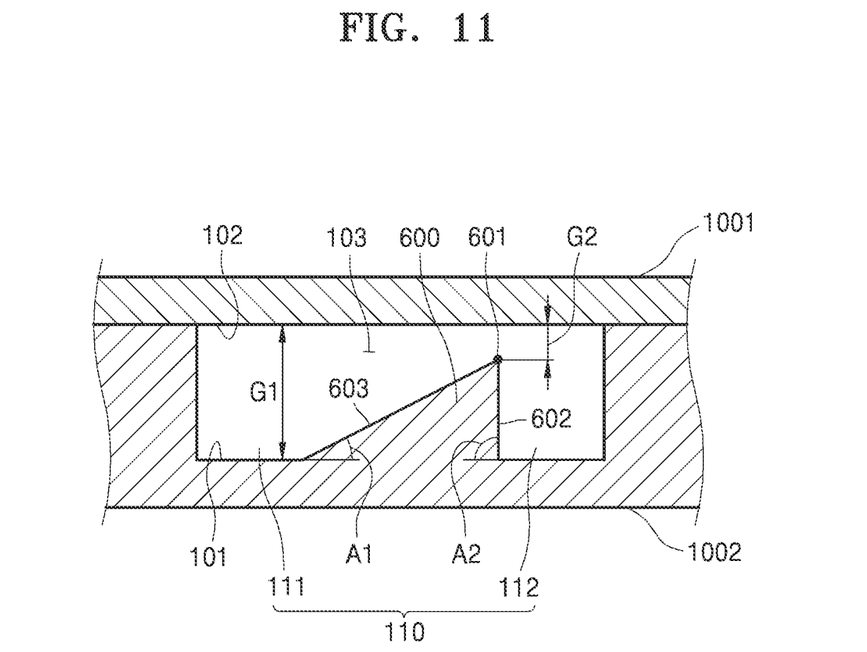
FIG. 11 is a cross-sectional view taken along line E-E' of FIG. 2.

FIG. 11 is a cross-sectional view taken along line E-E' of FIG. 2. Referring to FIG. 11, the barrier wall 600 may extend from a lower wall 101 of the sample chamber 100 toward an upper wall 102 thereof. The sample chamber 100 is divided by the barrier wall 600 into an inner region 111 that is located close to the rotation center RC in the radial direction and an outer region 112 that is located away from the rotation center RC. The barrier wall 600 forms a bottleneck portion 103 with the upper wall 102. The inner region 111 is connected to the outer region 112 by the bottleneck portion 103. Although not shown, the barrier wall 600 may extend from the upper wall 102 of the sample chamber 100 toward the lower wall 101 thereof and form the bottleneck portion 103 with the lower wall 101.

During the centrifugation of the sample in the sample chamber 100 to discharge the upper material layer (for example, a plasma layer in a blood sample) of the layers in the sample chamber 100, the sample moves from the inner region 111 to the outer region 112 across the bottleneck portion 103 by a centrifugal force so that the sample is separated into a plurality of layers by a density gradient within the sample chamber 100. When the microfluidic apparatus 1 is stopped from rotating, i.e., when a centrifugal force is no longer present, the bottleneck portion 103 serves to restrict movement of the sample between the inner region 111 and the outer region 112. In other words, a flow of the fluid in the radial direction is restricted by the barrier wall 600 in the sample chamber 100, and thus, mixing of the layers separated from each other by the centrifugation will be reduced or prevented. An inner gap G1 and an outer gap G2 of the bottleneck portion 103 that are distances between the bottom neck portion 103 and the upper wall 102 are greater than a gap that can cause a capillary action so as to allow movement of the fluid through the bottleneck portion 103. When the capillary action occurs at the bottleneck portion 103, the bottleneck portion 103 may be clogged to prohibit movement of the fluid during the centrifugation. In the microfluidic apparatus 1 according to the present embodiment, the inner and outer gaps G1 and G2 of the bottleneck portion 103 are greater than a gap that can induce a capillary action, thereby facilitating smooth movement of the fluid from the inner region 111 to the outer region 112 by a centrifugal force during centrifugation. Furthermore, after the centrifugation, the movement of the fluid between the inner region 111 and the outer region 112 may be partially restricted due to the narrow inner and outer gaps G1 and G2.

Centrifugation facilitates movement of the sample from the inner region 111 to the outer region 112. To achieve this, the barrier wall 600 may be formed so that the bottleneck portion 103 becomes narrower from an inner portion of the sample chamber 100 to an outer portion of the sample chamber 100 as shown in FIG. 11. In other words, a path of a fluid formed by the bottleneck portion 103 may have the inner gap G1 wider than the outer gap G2. Since the sample flows from the inner region 111 to the outer region 112 by centrifugal force during centrifugation, the sample can easily pass through the bottleneck portion 103 and then move to the outer region 112 due to the wide inner gap G1. On the other hand, when the microfluidic apparatus 1 is stopped from rotating, i.e., in the absence of a centrifugal force, the sample cannot easily pass through the bottleneck portion 103 due to the narrow outer gap G2. Thus, this structure may facilitate movement of the sample from the inner region 111 to the outer region 112 during centrifugation while limiting a flow of the sample from the outer region 112 to the inner region 111 when the microfluidic apparatus 1 is stopped. The barrier wall 600 for forming the bottleneck portion 103 may have a triangular cross-sectional shape that has an apex 601 as shown in FIG. 11. In this case, a leg 602 of the apex 601 at the outer region 112 has a larger inclination angle A2 than an inclination angle A1 of a hypotenuse 603 at the inner region 111. This structure may restrict a flow of the sample from the outer region 112 to the inner region 111 more easily. Furthermore, since no step height difference exists between the hypotenuse 603 and the lower wall 101 of the inner region 111, this may further facilitate a smooth flow of the sample from the inner region 111 to the outer region 112 during the centrifugation.

Figure 12:
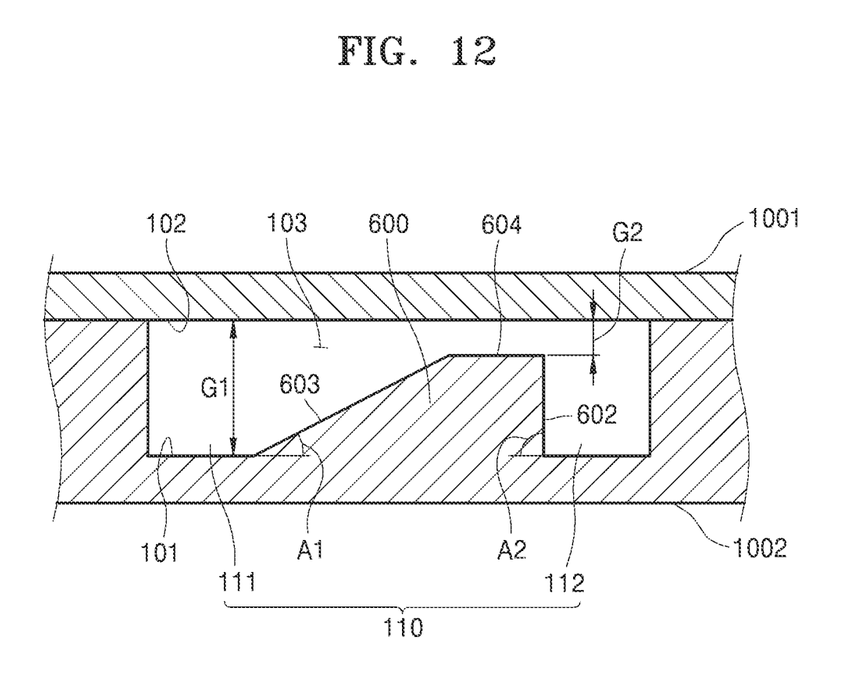
FIG. 12 is a cross-sectional view of another example of a bottleneck portion taken along line E-E' of FIG. 2.

Although the barrier wall 600 has a triangular cross-sectional shape as shown in FIG. 11, the present invention is not limited thereto. Referring to FIG. 12, the barrier wall 600 may have a trapezoidal cross-sectional shape that, together with the bottom surface to which it is attached, has a vertical wall 602 perpendicular to the upper wall 102, a hypotenuse 603, and a top side 604 parallel to the upper wall 102. The barrier wall 600 may have various other shapes as long as a minimum gap of the bottleneck portion 103 is greater than a gap that can cause a capillary action.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A microfluidic apparatus that induces centrifugal fluid-flow when rotated, the microfluidic apparatus comprising:
    a separation unit that separates a target cell from a sample;
    a recovery chamber connected to the separation unit through a recovery channel, which chamber accommodates a target cell obtained from the separation unit;
    an upper plate and a lower plate forming, respectively, an upper wall and a lower wall of the recovery chamber;

and, optionally, a partition plate sandwiched between the upper and lower plate and forming a side wall of the recovery chamber; and an inclined portion disposed in the recovery chamber and tilted toward a bottom of the recovery chamber along a direction of the centrifugal force, wherein:

the inclined portion is a protrusion extending into the recovery chamber from a bottom surface of the upper plate;

or the inclined portion is disposed on the partition plate inside the recovery chamber.

2. The microfluidic apparatus of claim 1, wherein the inclined portion is disposed at a location within the recovery chamber corresponding to an entrance of the recovery channel to the recovery chamber.

3. The microfluidic apparatus of claim 2, wherein the inclined portion has a width greater than or equal to a width of the recovery channel.

4. The microfluidic apparatus of claim 1, wherein the microfluidic apparatus comprises a partition plate forming a side wall of the recovery chamber, and the inclined portion is disposed on the partition plate.

5. The microfluidic apparatus of claim 1, further comprising a cover that covers an opening in an upper portion of the recovery chamber and is configured to open the recovery chamber when removed from the microfluidic apparatus.

6. The microfluidic apparatus of claim 5, wherein a connection port is disposed in the upper plate, the port providing an opening to the recovery chamber, and wherein the cover is removably coupled to the upper plate so as to cover the connection port.

7. The microfluidic apparatus of claim 6, wherein the cover has a groove recessed from a bottom surface thereof, and wherein one end of the groove extends to an edge of the microfluidic apparatus.

8. The microfluidic apparatus of claim 1, wherein the separation unit comprises:

a sample chamber configured to supply a fluid containing a target material in which fine beads are bound to the target cell in the sample; and a separation chamber configured to accommodate a density gradient medium (DGM) and to receive the fluid from the sample chamber to separate the target material from the fluid based on density.

9. The microfluidic apparatus of claim 8, wherein the target cell includes a circulating tumor cell (CTC), a cancer stem cell, or a cancer cell.

10. A microfluidic apparatus that induces a flow of a fluid due to a centrifugal force when rotated, the microfluidic apparatus comprising:

a separation unit that separates a target cell from a sample;

a recovery chamber connected to the separation unit through a recovery channel, which chamber accommodates a target cell obtained from the separation unit;

a cover that covers an upper portion of the recovery chamber and is removable so as to open the upper portion of the recovery chamber; and an upper plate forming an upper wall of the recovery chamber, wherein a connection port is disposed in the upper plate and provides an opening to the recovery chamber, and the cover is removably coupled to the upper plate so as to cover the connection port, wherein the cover has a groove recessed in a bottom surface thereof, and one end of the groove extends to an edge of the microfluidic apparatus.

11. The microfluidic apparatus of claim 10, further comprising an inclined portion that is disposed in the recovery chamber so as to guide a target cell introduced into the recovery chamber through the recovery channel towards a bottom of the recovery chamber upon application of centrifugal force by rotation of the microfluidic apparatus.

12. The microfluidic apparatus of claim 11, wherein the inclined portion is a protrusion extending from the bottom surface of the cover through the connection port and is disposed inside the recovery chamber.

13. The microfluidic apparatus of claim 10, wherein the separation unit comprises:

a sample chamber configured to supply a fluid containing a target material in which fine beads are bound to the target cell in the sample; and a separation chamber configured to accommodate a density gradient medium (DGM) and to receive the fluid from the sample chamber to separate the target material from the fluid based on density.

14. The microfluidic apparatus of claim 13, wherein the target cell includes a circulating tumor cell (CTC), a cancer stem cell, or a cancer cell.

* * * * *